United States Patent [19]

Wielinger et al.

[11] 4,199,550

[45] Apr. 22, 1980

[54] DEVICE FOR THE UNIFORM DOSING OF FAECAL MATTER FOR COMPONENT DETECTION

[75] Inventors: Hans Wielinger; Walter Rittersdorf, both of Mannheim-Waldhof, Fed. Rep. of Germany

[73] Assignee: Boehringer Mannheim GmbH, Mannheim-Waldhof, Fed. Rep. of Germany

[21] Appl. No.: 917,718

[22] Filed: Jun. 21, 1978

[30] Foreign Application Priority Data

Jul. 2, 1977 [DE] Fed. Rep. of Germany ....... 2729924

[51] Int. Cl.² ........................................... G01N 33/16
[52] U.S. Cl. .................................. 422/58; 23/230 B; 422/56
[58] Field of Search .................... 422/56, 58, 99, 104; 23/230 B

[56] References Cited

U.S. PATENT DOCUMENTS

| 3,891,507 | 6/1975 | Breuer | 23/230 B X |
|---|---|---|---|
| 3,915,647 | 10/1975 | Wright | 23/230 B X |
| 3,990,850 | 11/1976 | Friedman et al. | 23/230 B |
| 3,996,006 | 12/1976 | Pagano | 23/253 TP |
| 4,092,120 | 5/1978 | Suovaniemi et al. | 23/230 B X |

*Primary Examiner*—Arnold Turk
*Attorney, Agent, or Firm*—Sprung, Felfe, Horn, Lynch & Kramer

[57] ABSTRACT

A device for the uniform dosing of an amount of faeces onto reagent paper for the detection of a component material in the faeces. The device comprises test paper and a template disposed thereover having a given thickness and comprising at least one set of two superposed openings of any desired shape. Each set of openings includes a first opening and a second opening disposed between the first opening and the test paper and having a larger area than and encompassing the area of the first opening.

7 Claims, 4 Drawing Figures

U.S. Patent     Apr. 22, 1980     4,199,550
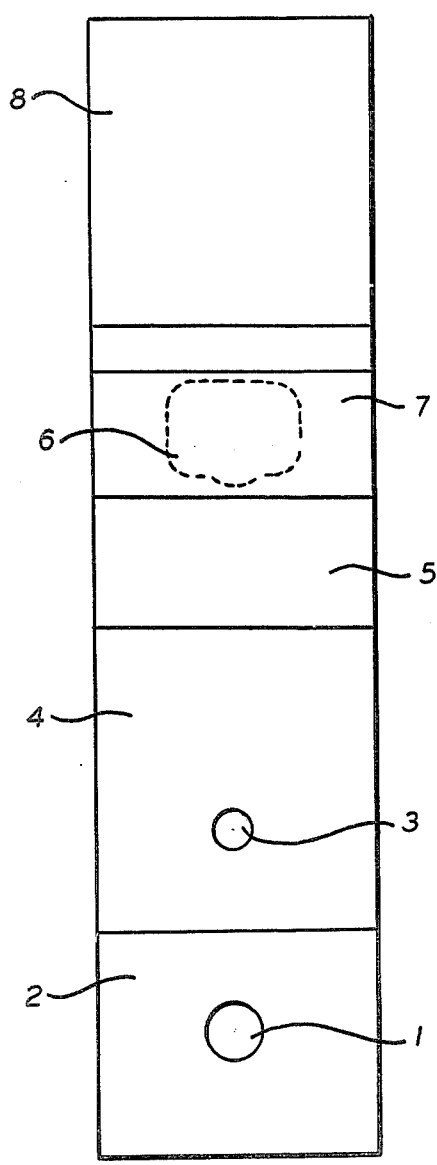
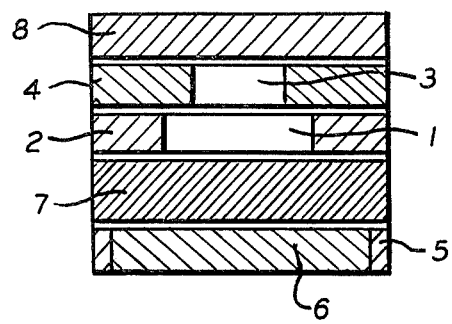
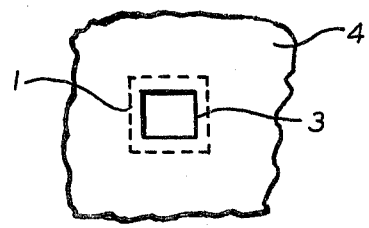
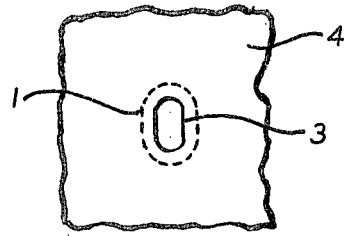

DEVICE FOR THE UNIFORM DOSING OF FAECAL MATTER FOR COMPONENT DETECTION

BACKGROUND OF THE INVENTION

The present invention relates to a device for the uniform dosing of amounts of faeces onto reagent papers.

The recognition of component materials in faeces, especially of blood, has recently achieved increasing importance, for example in the case of control investigations. For this purpose, test papers containing guaiac resin as an indicator have proved to be particularly useful.

For the detection of blood in faeces, the latter are applied to a reagent paper and, after drying, development is carried out with an alcoholic solution of hydrogen peroxide. The reagent papers are either supplied in the form of rolls or are struck into pieces of cardboard provided with an opening for the introduction of the faeces.

In practice, it has been found that, even in the case of a precise description of the manner in which the faeces are to be dosed, even well trained operators have great difficulty in applying standardized amounts of faeces to the test paper in order to achieve reproducible results.

Investigations have now shown that the sensitivity of the test papers depends decisively upon the amount of faeces applied, which is not surprising since the exactitude of an analytical method depends, in the first place, upon the dosing of the sample.

In the case of commercially available diagnostic agents for determining the component materials of body fluids, a uniform sample dosing does not give rise to any difficulties. As is well known, it is ensured by the take up of fluid by the test area.

In the case of faeces, however, because of the viscosity thereof, which is higher than that of body fluids, the amount of sample must be applied by the user directly to the reagent paper. Therefore, a continuously uniform dosing is not ensured. It would be obvious to cover test papers for the detection of component materials of faeces with a device which is to be filled with faeces. This device must be constructed in such a manner that, in the course of filling, the user is more or less obliged to apply a standardized amount of faeces. For example, this may be a template provided with a circular opening which thus has a cylindrical shape. Models have been devloped but, in practice, it has been found that such models are not suitable, for example, for the conventional testing of faeces.

As is also known, in the case of methods for the detection of blood in faeces with the help of reagent papers, the sample must be developed with an alcoholic solution of hydrogen peroxide which is applied dropwise to the rear side of the coated paper. In the course of the development process, the chromogen present in the reagent paper is oxidized by the catalytic action of the hemoglobin in the blood to give a blue-colored material. The colored material chromatographs out from the faecal sample, depending upon the shape of the faecal sample, are more or less irregular and appear to the observer as one or more blue zones. If, over the test paper, there is applied a second and somewhat thicker layer of paper, for example cardboard, in which is stamped a circular opening, then a cylinder is provided which is filled with the faeces to be investigated. In this way, while the user always applies a uniform amount of the faeces to be investigated, it has been found that the color development, in comparison with a detection test in which the same amount of the same faeces is employed but without the cylinder, is considerably inhibited and the reaction appears, therefore, to be insensitive.

SUMMARY OF THE INVENTION

It is therefore an object of the present invention to provide a device which makes it possible, even for untrained persons, to apply faeces of varying consistency in a standardized and uniform amount to a reagent paper without this process influencing the maximum achievable sensitivity of the reagent paper.

Another object is to provide a device which does not suffer from the disadvantages of the known devices.

Thus, according to the present invention, there is provided a device for the uniform dosing of amounts of faeces onto reagent papers for the detection of the component materials of the faeces, comprising a test paper and a template arranged thereabove and provided with an opening of any desired shape, the template comprising two layers of a solid material, the layer which lies directly on top of the reagent paper having a larger opening than the other layer.

The device according to the present invention can be produced in the following manner:

A reagent paper for the detection of blood in faeces is laid on a layer of a material with an opening of any desired shape. Over this first layer is laid a second layer with an opening which can also have any desired shape but which, in comparison with the first opening, is smaller.

The solid material used is preferably cardboard with a surface weight of 200–400 g./m$^2$, the openings preferably being circular or rectangular. The elements can be affixed to each other by any suitable adhesive for the materials used.

The device thus produced has the advantage that the user, when he fills the opening which he can see with faeces, independently of the consistency of the faeces, he always applies the same amount of sample to the reagent paper. In addition, this arrangement has, surprisingly, the following effect: in the case of the development of the sample with an alcoholic solution of hydrogen peroxide, the evaluator is given a clear color reaction going uniformly outwardly from the faecal sample in a manner which cannot be achieved with any previously known model.

BRIEF DESCRIPTION OF THE DRAWING

FIG. 1 is a top exploded view of a device according to the present invention;

FIG. 2 is a sectional view of the embodiment shown in FIG. 1; and

FIGS. 3A and 3B are top views of alternate embodiments of the invention.

DETAILED DESCRIPTION OF THE INVENTION

Referring now to FIGS. 1-3, which illustrate some embodiments of the invention, the following Examples are given for the purpose of illustrating the present invention.

EXAMPLE 1

Small folder for the detection of blood in faeces

Two circular openings 1 and 3 are stamped out from cardboard layers 2 and 4 respectively with a surface weight of 250 g/m². Opening 1 has a diameter of 1.3 cm. and opening 3 a diameter of 0.8 cm. An areea 6 is pre-stamped with perforations on a cardboard base sheet 5, so that it can subsequently be torn out without difficulty. Onto the base sheet 5, a reagent paper 7 is affixed, along the longer edge of sheet 5 in such a manner that the reagent paper 7 comes to lie over at least the area 6. Layer 2 is affixed to layer 4 and with openings 1 and 3 aligned in such a manner that opening 3 is enveloped by opening 1 and the two openings overlie the area 6. The two layers 2,4 are superposed on base sheet 5 and reagent paper 7 with layer 2 closest thereto. The reagent paper 7 is affixed along the side edge of the layer 2. The openings 1 and 3 also thereby lie over the reagent paper 7. Finally, a cardboard cover member 8 is laid in such a manner that it lies over layer 4.

In order to use the reagent paper, the cover 8 is lifted off and a small amount of faeces is introduced into the opening 3 and spread with a spatula. The faeces is thereby pressed in the shape of a cylinder with the diameter of the opening 3, 0.8 cm., into the opening 1 and comes into close contact with the reagent paper 7.

By means of this procedure, it is possible always to dose the same amount of faeces. After drying the faeces, the perforated area 6 is torn off along the perforation and the reagent paper 7 treated with droplets from the now exposed side with a 3% ethanolic solution of hydrogen peroxide. When blood is present in the faeces, a uniform blue ring is formed around the faecal sample, the extent of which corresponds approximately to the difference of the radii of the openings 1 and 3.

EXAMPLE 2

Small folder for the detection of blood in faeces for two analysis samples

It has proved to be practical to take two samples from a quantity of faeces at points at a distance from one another. In order to do this, the small folder described in Example 1 can be constructed in such a manner that, instead of one set of aligned openings, it has two sets of aligned openings which lie close together with the corresponding reagent paper and aligned perforated area. The small folder is otherwise produced in the same manner as described in Example 1. On to such a small folder, there are applied two faecal samples from points of the faeces which are spaced apart. Since the blood in the faeces is, depending upon the nature of the hemorrhage, different (more or less homogeneous), taking samples from two points removed from one another provides a surer assessment than taking only one sample.

EXAMPLE 3

Small folder for the detection of blood in faeces

For the application of especially hard faeces, the following embodiment has proved to be especially suitable:

Into a cardboard with a surface weight of 300 g./m², there are stamped, instead of the circular holes for openings 1 and 3 illustrated in FIG. 1, oval or rectangular openings shown in FIGS. 3B and 3A respectively, with the axis length of the openings having a ratio of 6:5 and the longitudinal axis of the opening 1 being 1.4 cm. and that of the opening 3 being 0.9 cm. The small folder is otherwise produced in precisely the same manner as described in Examples 1 and 2.

What is claimed is:

1. A device for the uniform dosing of an amount of faeces onto reagent paper for the detection of a component material in the faeces, comprising a test paper for detecting a component material in faeces and a template disposed over one surface of the test paper and having a given thickness and comprising at least one set of two superposed openings, each set comprising a first opening and a second disposed between the first opening and the test paper and having a larger area than and encompassing the area of the first opening.

2. The device according to claim 1, wherein the template comprises a first layer having each first opening therein and a second layer having each second opening therein and disposed between the first layer and the test paper.

3. The device according to claim 2, wherein the layers each comprise cardboard with a surface weight of 200 to 400 g./m².

4. The device according to claim 1, wherein the openings have a circular shape.

5. The device according to claim 1, wherein the openings have one of an oval or rectangular shape.

6. The device according to claim 2, further comprising a base sheet disposed on the other surface of the test paper and a cover member disposed over the first layer.

7. The device according to claim 6, wherein the base sheet has a removable portion aligned with each second opening to expose the other surface of the test paper.

* * * * *